United States Patent
Nakamoto et al.

(10) Patent No.: US 9,276,289 B2
(45) Date of Patent: Mar. 1, 2016

(54) AMBIENT TEMPERATURE MOLTEN SALT, ELECTRODE, BATTERY, AGENT FOR PREVENTING CHARGE-UP, AND METHOD FOR OBSERVING SAMPLE

(75) Inventors: Hirofumi Nakamoto, Susono (JP); Fuminori Mizuno, Susono (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 3 days.

(21) Appl. No.: 13/515,689

(22) PCT Filed: Oct. 22, 2010

(86) PCT No.: PCT/JP2010/068721
§ 371 (c)(1),
(2), (4) Date: Aug. 8, 2012

(87) PCT Pub. No.: WO2011/074325
PCT Pub. Date: Jun. 23, 2011

(65) Prior Publication Data
US 2013/0084491 A1    Apr. 4, 2013

(30) Foreign Application Priority Data
Dec. 16, 2009   (JP) .................... PCT/JP2009/070985

(51) Int. Cl.
*H01M 10/056* (2010.01)
*C07D 233/10* (2006.01)
(Continued)

(52) U.S. Cl.
CPC .......... *H01M 10/056* (2013.01); *C07D 233/10* (2013.01); *H01B 1/122* (2013.01); *H01J 37/26* (2013.01); *H01M 4/136* (2013.01); *H01M 4/58* (2013.01); *H01M 10/0525* (2013.01); *H01M 10/0565* (2013.01); *H01M 2300/0022* (2013.01); *H01M 2300/0045* (2013.01); *Y02E 60/122* (2013.01)

(58) Field of Classification Search
None
See application file for complete search history.

(56) References Cited

U.S. PATENT DOCUMENTS

2004/0170890 A1* 9/2004 Matsunaga et al. ........... 429/137
2005/0175867 A1* 8/2005 Adachi et al. .................. 429/12

(Continued)

FOREIGN PATENT DOCUMENTS

| | | |
|---|---|---|
| CN | 101278366 A | 10/2008 |
| JP | A-62-165879 | 7/1987 |

(Continued)

OTHER PUBLICATIONS

Wicelinski et al., "Low Temperature Chlorogallate Molten Salt Systems", J. Electrochem. Soc., Jan. 1, 1987, vol. 134, Issue 1, pp. 262-263.*

(Continued)

*Primary Examiner* — Ula C Ruddock
*Assistant Examiner* — Osei Amponsah
(74) *Attorney, Agent, or Firm* — Oliff PLC (57) ABSTRACT

An object of the present invention is to provide an ambient temperature molten salt having excellent electron conductivity in addition to ion conductivity. The present invention attains the object by providing an ambient temperature molten salt including a first imidazolium salt having a cationic segment represented by the general formula (1) and an anionic segment represented by $MX_4$ (where M is a transition metal and X is a halogen); and a second salt having a cationic segment as a monovalent cation and an anionic segment as a halogen.

11 Claims, 4 Drawing Sheets (51) Int. Cl.
  *H01B 1/12* (2006.01)
  *H01J 37/26* (2006.01)
  *H01M 4/136* (2010.01)
  *H01M 4/58* (2010.01)
  *H01M 10/0525* (2010.01)
  *H01M 10/0565* (2010.01)

(56) References Cited

U.S. PATENT DOCUMENTS

| 2005/0288484 | A1* | 12/2005 | Holbrey et al. ............... 528/480 |
| 2007/0129568 | A1* | 6/2007 | Flanagan et al. ............... 562/410 |
| 2008/0241705 | A1* | 10/2008 | Wakita et al. ............... 429/344 |
| 2009/0034161 | A1 | 2/2009 | Takeda et al. |
| 2009/0173882 | A1 | 7/2009 | Kuwabata et al. |

FOREIGN PATENT DOCUMENTS

| JP | A-2001-243995 | 9/2001 |
| JP | A-2002-110230 | 4/2002 |
| JP | A-2002-176188 | 6/2002 |
| JP | A-2008-218384 | 9/2008 |
| JP | A-2009-218005 | 9/2009 |
| WO | WO 03/106419 A1 | 12/2003 |
| WO | WO 2007/083756 A1 | 7/2007 |

OTHER PUBLICATIONS

Zhang, Q. et al., *Studies on an ionic liquid based on $FeCl_3$ and its properties*, Fluid Phase Equilibria, 2004, vol. 226, pp. 207-211.

Yoshida, Y. et al., *Conducting and Magnetic Properties of 1-Ethyl-3-methylimidazolium (EMI) Salts Containing Paramagnetic Irons: Liquids [EMI] [$M^{III}Cl_4$] ($M=Fe$ and $Fe_{0.5}Ga_{0.5}$) and Solid $[EMI]_2[Fe^{II}Cl_4]$*, Bull. Chem. Soc. Jpn., 2005, vol. 78, pp. 1921-1928.

Castro, S. et al., Effect of liquid properties on electrosprays from externally wetted ionic liquid ion sources, Journal of Applied Physics, 2007, vol. 102, pp. (094310-1)-(094310-5).

Dec. 7, 2010 International Search Report issued in International Patent Application No. PCT/JP2010/068721.

* cited by examiner

AMBIENT TEMPERATURE MOLTEN SALT, ELECTRODE, BATTERY, AGENT FOR PREVENTING CHARGE-UP, AND METHOD FOR OBSERVING SAMPLE

TECHNICAL FIELD

The present invention relates to an ambient temperature molten salt having excellent electron conductivity in addition to ion conductivity.

BACKGROUND ART

An ambient temperature molten salt is a generic name for salts which exist in a liquid state around ambient temperature (ambient temperature), and imidazolium-based, pyridium-based, alicyclic amine-based, aliphatic amine-based and aliphatic phosphonium-based are known as kinds of a cationic segment. Further, it is known that, because of its excellent nonvolatility and voltage endurance, an ambient temperature molten salt is used as an electrolyte of an electrochemical device. For example, in Patent Literature 1, a secondary battery provided with positive and negative electrodes, at least one electrode of which is a conductive polymer, and a liquid electrolyte composed of an ambient temperature molten salt is disclosed.

Further, in Patent Literature 2, there is disclosed an all-solid lithium secondary battery, in which an ionic liquid (an ambient temperature molten salt) having 1-ethyl-3-methylimidazolium as a cationic segment exists in a pinhole of a solid electrolyte layer. This technique is intended for preventing an internal short circuit of the battery by having the ionic liquid exist in a pinhole of the solid electrolyte layer.

On the other hand, it is known that an ambient temperature molten salt is used as an agent for preventing a charge-up, which prevents an electric charge from building up in a measuring object during measurement by an electron microscope. For example, in Patent Literature 3, an agent for preventing a charge-up for an electron microscope with the use of an ionic liquid (an ambient temperature molten salt) is disclosed. 'Charge-up' generally signifies a phenomenon such that an appropriate result is not obtained for the reason that a measuring object (such as an insulator) becomes charged during measurement with the use of electron rays or the like. For example, in measurement with the use of a scanning electron microscope (SEM), in the case where a secondary electron emission amount is more than a primary electron incidence amount, occasionally, a measuring object becomes positively charged during the measurement and an obtained display of a whole SEM image may become white in some occasion.

CITATION LIST

Patent Literature

Patent Literature 1: Japanese Patent Application Publication Laid-Open (JP-A) No. S62-165879
Patent Literature 2: JP-A No. 2009-218005
Patent Literature 3: International Publication No. 2007/083756

SUMMARY OF INVENTION

Technical Problem

An ambient temperature molten salt is useful as an electrolyte of an electrochemical device by reason of having predetermined ion conductivity, as described above. However, a conventional ambient temperature molten salt has had little electron conductivity while having ion conductivity. In other words, a conventional ambient temperature molten salt has been utilizable as an electrolyte of an electrochemical device by reason of having little electron conductivity and having only ion conductivity. On the other hand, an ambient temperature molten salt becomes very useful as a material to be added to an electrode if it has electron conductivity in addition to ion conductivity, for example. However, conventionally, an ambient temperature molten salt having ion conductivity and electron conductivity together has not been known.

Further, in the case where a conventional ambient temperature molten salt is used as an agent for preventing a charge-up for an electron microscope, the ambient temperature molten salt may prevent the charge-up at some level by reason of being high in ion concentration and having ion conductivity. However, there is a problem in that since a conventional ambient temperature molten salt has little electron conductivity, the effect of preventing a charge-up is low. Thus, in a long-time continuous measurement, there is a problem in that an electric charge builds up in a measuring object to cause a charge-up.

The present invention has been made in view of the above-mentioned actual circumstances, and the main object thereof is to provide an ambient temperature molten salt having excellent electron conductivity in addition to ion conductivity.

Solution to Problem

In order to achieve the object, the present invention provides an ambient temperature molten salt comprising: a first imidazolium salt having a cationic segment represented by the following general formula (1) and an anionic segment represented by $MX_4$ (where M is a transition metal and X is a halogen); and a second salt having a cationic segment as a monovalent cation and an anionic segment as a halogen.

[Chemical Formula 1]

General Formula (1)

In the general formula (1), $R_1$ and $R_2$ are each an alkyl group with a carbon number of 1 to 10.

According to the present invention, the use of the first imidazolium salt and the second salt allows an ambient temperature molten salt to have excellent electron conductivity in addition to ion conductivity. Further, the ambient temperature molten salt of the present invention is so excellent in electron conductivity that it is also usable as a substitute for a conductive material (such as a carbon material) contained in a conventional electrode, for example.

In the invention, the M is preferably at least one kind selected from the group consisting of Fe, Cr and V. The reason therefor is that an ambient temperature molten salt is made to have excellent electron conductivity.

In the invention, it is preferable that the $R_1$ be an ethyl group and the $R_2$ a methyl group. The reason therefor is that they may allow an ambient temperature molten salt further favorable in electron conductivity.

In the invention, the second salt is preferably a second imidazolium salt having a cationic segment represented by the following general formula (2) and an anionic segment as a halogen. The reason therefor is that the second imidazolium salt singly has no electron conductivity ordinarily, but a combination thereof with the first imidazolium salt, which similarly having no electron conductivity singly, may improve electron conductivity.

[Chemical Formula 2]

General Formula (2)

In the general formula (2), $R_3$ and $R_4$ are each an alkyl group with a carbon number of 1 to 10.

In the invention, it is preferable that the $R_3$ be an ethyl group and the $R_4$ a methyl group. The reason therefor is that they may allow an ambient temperature molten salt which is further favorable in electron conductivity.

In the invention, the M is preferably Fe.

In the invention, the second salt is preferably a second metal salt having a cationic segment as an alkali metal and an anionic segment as a halogen. The reason therefor is that a combination of the second salt and the first imidazolium salt may improve electron conductivity.

In the invention, the alkali metal is preferably Li. The reason therefor is that it may allow an ambient temperature molten salt which is further favorable in electron conductivity.

In the invention, the halogen of the first imidazolium salt and the halogen of the second salt are preferably Br or Cl.

In the invention, the second salt is preferably contained at a ratio of 100 parts by mol or less in the case where the first imidazolium salt is regarded as 100 parts by mol. The reason therefor is that if a ratio of the second salt is too large, deterioration in electron conductivity is caused promptly, thus it is likely to give an ambient temperature molten salt which is low in electron conductivity from the beginning.

In the invention, the second salt is preferably contained at a ratio of 1 part by mol or more in the case where the first imidazolium salt is regarded as 100 parts by mol. The reason therefor is that if a ratio of the second salt is too small, the electron conductivity becomes the same electron conductivity as in the case of the first imidazolium salt alone, thus it is likely to bring a possibility of not improving electron conductivity.

Further, the present invention provides an electrode comprising the above-described ambient temperature molten salt.

According to the present invention, the use of the above-described ambient temperature molten salt allows an electrode excellent in not merely ion conductivity but also electron conductivity.

In the invention, an active material capable of supplying or receiving a metal ion is preferably further contained. The reason therefor is that this can prevent an electron conduction path from being cut by expansion or contraction of the active material.

Further, the present invention provides a cell comprising a first electrode, a second electrode, and an electrolyte layer formed between the first electrode and the second electrode, characterized in that at least one of the first electrode and the second electrode is the electrode, and the electrolyte layer does not transmit the ambient temperature molten salt contained in the electrode.

According to the present invention, the use of the above-described electrode containing the ambient temperature molten salt allows a cell small in internal resistance.

In the invention, the electrolyte layer is preferably a solid electrolyte layer having such denseness that does not allow the ambient temperature molten salt to transmit. The reason therefor is that it may allow a battery high in safety.

Further, the present invention provides an agent for preventing a charge-up comprising the above-described ambient temperature molten salt.

According to the present invention, the inclusion of the above-described ambient temperature molten salt allows an agent for preventing a charge-up to have excellent electron conductivity. Thus, the effect of preventing a charge-up is high, and building up an electric charge in a measuring object and occurrence of a charge-up can be prevented even in a case such as long-time continuous measurement.

In the invention, the agent for preventing a charge-up is preferably used for measurement by an electron microscope.

Further, the present invention provides a method for observing a sample, in which a sample having a measuring object and an agent for preventing a charge-up of the measuring object is observed by an electron microscope, characterized in that the agent for preventing a charge-up is the above-described agent for preventing a charge-up.

According to the present invention, the use of the above-described agent for preventing a charge-up may efficiently prevent a charge-up from occurring.

In the invention, the measuring object is preferably a member used for a battery.

Further, the present invention provides an electrode comprising a liquid electron/ion conductor and an active material capable of supplying or receiving a metal ion.

According to the present invention, the use of the liquid electron/ion conductor as a conductive assistant (a conductive material) may prevent an electron conduction path from being cut by expansion or contraction of the active material, and may improve cycling characteristics.

In the invention, the liquid electron/ion conductor is preferably an ambient temperature molten salt. The reason therefor is that it is excellent in nonvolatility and voltage endurance.

In the invention, the ambient temperature molten salt preferably comprises a first imidazolium salt having a cationic segment represented by the following general formula (1) and an anionic segment represented by $MX_4$ (where M is a transition metal and X is a halogen); and a second salt having a cationic segment as a monovalent cation and an anionic segment as a halogen. The reason therefor is that it is excellent in electron conductivity.

[Chemical Formula 3]

General Formula (1)

In the general formula (1), $R_1$ and $R_2$ are each an alkyl group with a carbon number of 1 to 10.

Advantageous Effects of Invention

The present invention produces the effect that an ambient temperature molten salt having excellent electron conductivity in addition to ion conductivity can be obtained.

DESCRIPTION OF EMBODIMENTS

An ambient temperature molten salt, an electrode, a battery, an agent for preventing a charge-up, and a method for observing a sample of the present invention are hereinafter described in detail.

A. Ambient Temperature Molten Salt

An ambient temperature molten salt of the present invention is first described. The ambient temperature molten salt of the present invention comprises: a first imidazolium salt having a cationic segment represented by the general formula (1) and an anionic segment represented by $MX_4$ (where M is a transition metal and X is a halogen); and a second salt having a cationic segment as a monovalent cation and an anionic segment as a halogen. In the general formula (1), $R_1$ and $R_2$ are each an alkyl group with a carbon number of 1 to 10.

According to the present invention, with the use of the first imidazolium salt and the second salt, the ambient temperature molten salt is made to have excellent electron conductivity in addition to ion conductivity. Further, the ambient temperature molten salt of the present invention is excellent in electron conductivity, therefore, it is also usable as a substitute for a conductive material (such as a carbon material) contained in a conventional electrode. Further, in particular, the first imidazolium salt or a second imidazolium salt (an example of the second salt) singly has no electron conductivity ordinarily. However, a combination thereof unexpectedly may allow electron conductivity to be dramatically improved. That is to say, an effect different in kind which may not be achieved by a single salt may be attained with a combination of the first imidazolium salt and the second imidazolium salt.

In the present invention, 'ambient temperature molten salt' is synonymous with an ionic liquid and signifies a salt with the melting point of 100° C. or less. Above all, the melting point of the ambient temperature molten salt of the present invention is preferably 80° C. or less, more preferably 40° C. or less, and far more preferably 25° C. (ambient temperature) or less.

Further, the ambient temperature molten salt of the present invention contains the above-described first imidazolium salt. The first imidazolium salt may be an ambient temperature molten salt itself or a solid salt at ambient temperature. That is to say, even though the first imidazolium salt is a solid salt at ambient temperature, it is only necessary that the ambient temperature molten salt may be obtained by coexisting with the second salt, for example. Further, in the present invention, $R_1$ and $R_2$ are each an alkyl group with a carbon number of 1 to 10, preferably an alkyl group with a carbon number of 1 to 4, above all. Specific examples of the alkyl group include an ethyl group, a methyl group, a propyl group and a butyl group. $R_1$ and $R_2$ may be either the same as or different from each other.

Above all, in the present invention, it is preferable that $R_1$ be an ethyl group and $R_2$ a methyl group. The reason therefor is that they may allow an ambient temperature molten salt which is further favorable in electron conductivity. Here, a cationic segment in which $R_1$ is an ethyl group and $R_2$ is a methyl group is 1-ethyl-3-methylimidazolium (EMIm).

Further, the first imidazolium salt has $MX_4$ (where M is a transition metal and X is a halogen) as an anionic segment. The M is not particularly limited if it is a transition metal, and preferably has plural valence states (such as plural valence states among monovalence, divalence, trivalence, quadrivalence and hexavalence. The reason therefor is that there is a possibility that valence modification of M causes electron conductivity to improve. Examples of M in the present invention include at least one kind selected from the group consisting of Fe, Cr, V, Co, Mn, Ti, Ru and Pb. Above all, the M is preferably at least one kind selected from the group consisting of Fe, Cr and V. On the other hand, examples of X in the present invention include F, Cl, Br and I, preferably Cl and Br, above all. The reason therefor is that it may allow the ambient temperature molten salt with low volatility, which is easily produced. Further, examples of valence of M element in $MX_4$ include divalence and trivalence, preferably trivalence, above all. Here, in the case where the valence of the M element is trivalence and the cationic segment is EMIm, the first imidazolium salt may be represented by $EMIm(M)X_4$. On the other hand, in the case where the valence of the M element is divalence and the cationic segment is EMIm, the first imidazolium salt may be represented by $[EMIm]_2MX_4$.

A method for producing the first imidazolium salt is not particularly limited if it is a method with which a desired first imidazolium salt can be obtained, and examples thereof include a method for mixing $MX_3$ with a raw material imidazolium salt which has a cationic segment represented by the general formula (1) and an anionic segment as a halogen. For example, in the case of obtaining $EMImFeCl_4$, EMImCl and $FeCl_3$ (Fe is trivalent) may be mixed at an equimolar ratio. On the other hand, in the case of obtaining $[EMIm]_2FeCl_4$, EMImCl and $FeCl_2$ (Fe is divalent) may be mixed at a molar ratio of 2:1.

Next, the second salt in the present invention is described. The second salt in the present invention has a cationic segment as a monovalent cation and an anionic segment as a halogen. The second salt may be an ambient temperature molten salt itself or a solid salt at ambient temperature. That is to say, even though the second salt is a solid salt at ambient temperature, it is only necessary that the ambient temperature molten salt may be obtained by coexisting with the first imidazolium salt, for example.

Further, the cationic segment in the second salt is ordinarily a monovalent cation. Examples of the cationic segment of the second salt include a cationic segment represented by the above-described general formula (2). In this case, the second salt in the present invention becomes a second imidazolium salt having a cationic segment represented by the general formula (2) and an anionic segment as a halogen. Further, $R_3$ and $R_4$ in the present invention are the same as the above-described $R_1$ and $R_2$; therefore, the description herein is omitted. Further, in the present invention, it is preferable that $R_3$ be the same as $R_1$, and $R_4$ the same as $R_2$.

Above all, in the present invention, it is preferable that $R_3$ be an ethyl group and $R_4$ a methyl group. The reason therefor is that they may allow an ambient temperature molten salt which is further favorable in electron conductivity. Here, a cationic segment in which $R_3$ is an ethyl group and $R_4$ is a methyl group is 1-ethyl-3-methylimidazolium (EMIm).

Further, other examples of the cationic segment of the second salt include an alkali metal. In this case, the second salt in the present invention becomes a second metal salt having a cationic segment as an alkali metal and an anionic segment as a halogen. Examples of the alkali metal include Li, Na and K, preferably Li, above all. The reason therefor is that it may allow the ambient temperature molten salt useful for a battery in which an Li ion is conducted. Further, Na and K may be made to be ambient temperature molten salts useful for a battery in which an Na ion and a K ion are conducted, respectively.

Further, the second salt has a halogen as an anionic segment. Examples of the halogen in the second salt include F, Cl, Br and I, preferably Cl and Br, above all. The reason therefor is that they allow the ambient temperature molten salt with low volatility, which is easily produced. Further, the halogen in the first imidazolium salt and the halogen in the second salt may be the same or different, preferably the same. A method for producing the second salt is not particularly limited if it is a method with which a desired second salt can be obtained. For example, the commercially available second salt may be used.

Further, the ratio of the first imidazolium salt and the second salt in the present invention is not particularly limited if it allows the ambient temperature molten salt to have desired electron conductivity. Above all, in the case where the first imidazolium salt is regarded as 100 parts by mol, the ratio of the second salt is preferably 100 parts by mol or less, more preferably 80 parts by mol or less, and far more preferably 50 parts by mol or less. The reason therefor is that if a ratio of the second salt is too large, deterioration in electron conductivity is promptly caused, thus it is likely to allow the ambient temperature molten salt to be low in electron conductivity from the beginning. On the other hand, the ratio of the second salt is preferably 1 part by mol or more, more preferably 5 parts by mol or more, and far more preferably 10 parts by mol or more. The reason therefor is that if a ratio of the second salt is too small, the electron conductivity becomes the same as in the case of the first imidazolium salt alone, thus it is likely to bring a possibility of not improving electron conductivity.

Further, electron conductivity (ambient temperature) of the ambient temperature molten salt of the present invention varies with kind and ratio of the first imidazolium salt and the second salt, and is preferably higher. Similarly, ion conductivity (ambient temperature) of the ambient temperature molten salt of the present invention also varies with kind and ratio of the first imidazolium salt and the second salt, and is preferably higher. Further, the ambient temperature molten salt of the present invention may be either the salt further having an ordinary solvent (water and organic solvent), or the salt having no ordinary solvent.

Further, uses of the ambient temperature molten salt of the present invention are not particularly limited, and examples thereof include an electrode additive to be added to an electrode of an electrochemical device. Examples of the electrochemical device include batteries such as a metal ion battery, a metal air battery, a fuel battery, and a solar battery. Further, the ambient temperature molten salt of the present invention is usable for secondary batteries in general (an Li-ion secondary battery and an NiH secondary battery). Further, the ambient temperature molten salt of the present invention is useful as an agent for preventing a charge-up.

B. Electrode

Next, an electrode of the present invention is described. The electrode of the present invention comprises the above-described ambient temperature molten salt.

According to the present invention, the use of the above-described ambient temperature molten salt allows the electrode excellent in not merely ion conductivity but also in electron conductivity.

Figure 1:
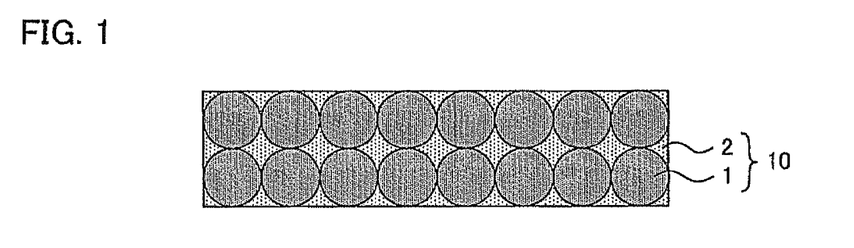
FIG. 1 is a schematic cross-sectional view showing an example of an electrode of the present invention.

FIG. 1 is a schematic cross-sectional view showing an example of the electrode of the present invention. An electrode 10 shown in FIG. 1 comprises an active material 1 capable of supplying or receiving a metal ion and an ambient temperature molten salt 2. The description of the ambient temperature molten salt used for the present invention is the same as those described in the 'A. Ambient temperature molten salt'; therefore, the description herein is omitted. Further, the content of the ambient temperature molten salt contained in the electrode varies greatly with kinds of the electrode and is not particularly limited.

The electrode of the present invention is not particularly limited as long as it has the ambient temperature molten salt, and may further contains at least one selected from the group consisting of the active material capable of supplying or receiving a metal ion, a catalyst for accelerating a reaction in the electrode, a conductive material having electron conductivity, an electrolyte material having ion conductivity (such as a solid electrolyte material), and a binder. As described above, since the ambient temperature molten salt used for the present invention has ion conductivity and electron conductivity, the ambient temperature molten salt may be used instead of at least one of the electrolyte material and the conductive material, and may be used in addition to the electrolyte material and the conductive material. In addition, the electrode of the present invention is ordinarily an electrode for an electrochemical device, above all, preferably an electrode for a battery, and more preferably an electrode for a metal ion battery, a metal air battery or a fuel battery. Further, the metal ion battery or the metal air battery may be a primary battery or a secondary battery.

Figure 2A:
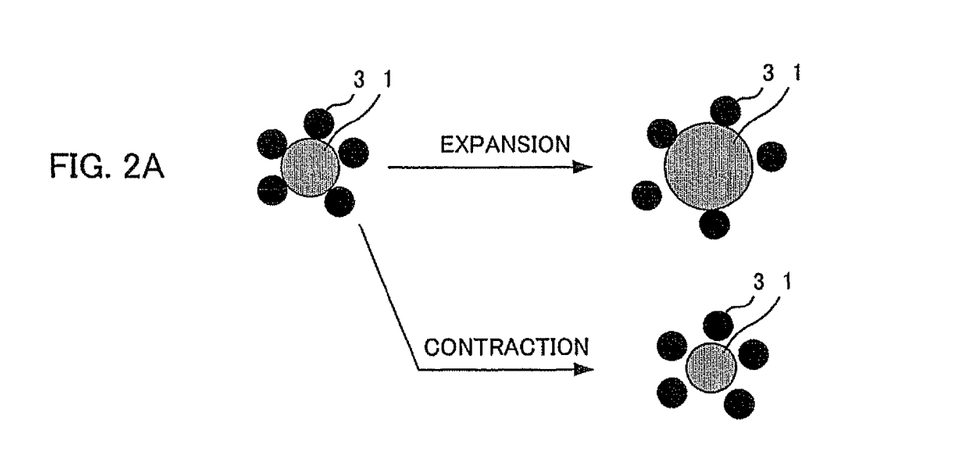
FIGS. 2A and 2B are each an explanatory view explaining the influence of expansion or contraction of an active material on an electron conduction path.

In particular, it is preferable that the electrode of the present invention further contains the active material capable of supplying or receiving a metal ion. The reason therefor is that that makes it capable of preventing an electron conduction path from being cut by expansion or contraction of the active material. This effect is described using FIGS. 2A and 2B. As shown in FIG. 2A, a conventional electrode has the active material 1 and a solid conductive material having electron conductivity (such as a carbon material) 3. Since the active material 1 itself ordinarily has no electron conductivity, the solid conductive material 3 is used for securing the electron conduction path in the electrode. Further, the active material 1 and the solid conductive material 3 form the electron conduction path by point-contacting with each other. Here, when the active material 1 expands by receiving a metal ion, the electron conduction path may occasionally be cut by being influenced by the expanded active materials 1. On the contrary, when the active material 1 contracts by supplying a metal ion, the electron conduction path may occasionally be cut by being influenced by the contraction of the active material 1. Thus, even in the case where the active material 1 expands or contracts, the electron conduction path formed between the active material 1 and the solid conductive material 3 becomes easily cut.

Figure 2B:
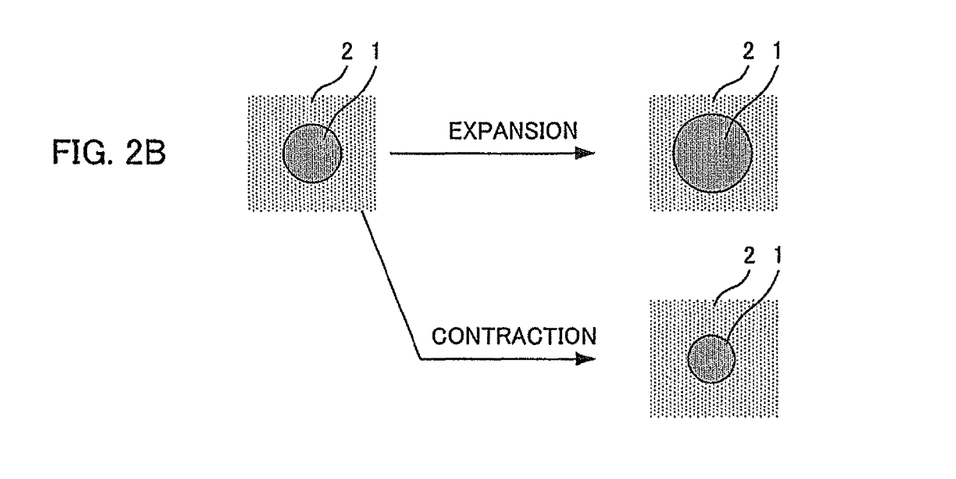

Meanwhile, as shown in FIG. 2B, the electrode of the present invention has the active material 1 and the ambient temperature molten salt 2 excellent in electron conductivity. Thus, even in the case where the active material 1 expands by receiving a metal ion, the electron conduction path will not be cut for the reason that the ambient temperature molten salt 2 as a liquid follows flexibly. Similarly, even in the case where the active material 1 contracts by supplying a metal ion, the electron conduction path will not be cut for the reason that the ambient temperature molten salt 2 as a liquid follows flexibly. Thus, the electron conduction path can be maintained by the flexible following of the ambient temperature molten salt 2 even in the case where volumetric change is caused in the active material 1. In addition, since the ambient temperature molten salt 2 has ion conductivity, an ion conduction path may be maintained even in the case where volumetric change is caused in the active material 1. Thus, both the electron conduction path and the ion conduction path are maintained, resulting in battery resistance to be restrained from increasing. Further, in the present invention, as shown in FIG. 2B, the ambient temperature molten salt 2 may be disposed so as to cover the whole surface of the active material 1. Because of that, the whole surface of the active material 1 may be utilized effectively, thus interface resistance may be decreased and the electrode suitable for, for example, high-speed charge and discharge may be made. In particular, in the case where the electrode of the present invention is an electrode for a secondary battery, the effect of the present invention may be sufficiently performed for the reason that expansion and contraction of the active material are repeated. In addition, in the case of using the insulating active material, the ambient temperature molten salt contacts with the insulating active material constantly, therefore, there is also the advantage of improving coulombic efficiency.

Further, the shape of the active material is not particularly limited and examples thereof include a powdery shape, a thin-film shape and a porous shape. In the case where the active material is of a powdery shape, the ambient temperature molten salt preferably exists in a void between particles of the active material. Further, in the case where the active material is of a porous shape, the ambient temperature molten salt preferably exists in a void of the porous shape. The ratio of the active material contained in the electrode is not particularly limited, and is preferably larger, for example, preferably 50% by weight or more, more preferably within a range of 80% by weight to 99% by weight.

Examples of the electrode containing the active material include a positive electrode and a negative electrode for the metal ion battery and a negative electrode for the metal air battery. A positive electrode (an air electrode) for the metal air battery ordinarily contains no active materials since the positive electrode uses air (oxygen) as a positive active material. Further, in the case where the electrode of the present invention is a positive electrode for the metal ion battery, examples of such a positive electrode include a positive electrode containing at least a positive active material and the ambient temperature molten salt and further at least one of a conductive material, an electrolyte material (such as a solid electrolyte material) and a binder as required. Further, in the case where the electrode of the present invention is a negative electrode for the metal ion battery or the metal air battery, examples of such a negative electrode include a negative electrode containing at least a negative active material and the ambient temperature molten salt and further at least one of a conductive material, an electrolyte material (such as a solid electrolyte material) and a binder as required.

Further, kinds of a metal ion in the metal ion battery and the metal air battery are not particularly limited and examples thereof include alkali metal ions such as Li ion, Na ion and K ion; alkaline-earth metal ions such as Mg ion and Ca ion; amphoteric metal ions such as Al ion and Zn ion; and transition metal ions such as Fe ion. Above all, in the present invention, the metal ion is preferably alkali metal ions or alkaline-earth metal ions, more preferably alkali metal ions, and particularly preferably Li ion. The reason therefor is that a battery with high energy density may be obtainable.

For example, in the case where the electrode of the present invention is a positive electrode for a lithium secondary battery, examples of an active material to be used (a positive active material) include $LiCoO_2$, $LiMnO_2$, $Li_2NiMn_3O_8$, $LiVO_2$, $LiCrO_2$, $LiFePO_4$, $LiCoPO_4$, $LiNiO_2$ and $LiNi_{1/3}CO_{1/3}Mn_{1/3}O_2$. Further, for example, in the case where the electrode of the present invention is a negative electrode for a lithium secondary battery, examples of an active material to be used (a negative active material) include a metal active material and a carbon active material. Examples of the metal active material include In, Al, Si, and Sn. On the other hand, examples of the carbon active material include mesocarbon microbeads (MCMB), high orientation property graphite (HOPG), hard carbon and soft carbon. Further, for example, in the case where the electrode of the present invention is a negative electrode for a lithium air battery, examples of an active material to be used include a lithium simplex, a lithium alloy, an oxide containing lithium and a nitride containing lithium. Examples of the lithium alloy include a lithium-aluminum alloy, a lithium-tin alloy, a lithium-lead alloy and a lithium-silicon alloy. Examples of the oxide containing lithium include a lithium-titanium oxide. Examples of the nitride containing lithium include a lithium-cobalt nitride, a lithium-iron nitride and a lithium-manganese nitride.

On the other hand, the electrode of the present invention may be an electrode that does not to contain the active material. Examples of the electrode containing no active materials include an air electrode for the metal air battery. The air electrode for the metal air battery uses air (oxygen) as an active material. Examples of the conventional air electrode include electrodes having a conductive material having electron conductivity, a catalyst, and an electrolyte material having metal ion conductivity. In the present invention, the ambient temperature molten salt may be used instead of at least one of the conductive material and the electrolyte material, and may be used in addition to the conductive material and the electrolyte material. The ambient temperature molten salt in the present invention is liquid at ambient temperature, therefore, oxygen is occasionally taken in the air electrode with difficulty, depending on the amount of the ambient temperature molten salt. In such a case, oxygen is preferably supplied by bubbling.

Further, other examples of the electrode containing no active materials include an electrode (an anode electrode and a cathode electrode) for a fuel battery. The conventional electrode for a fuel battery ordinarily has a conductive material having electron conductivity, an electrolyte material having proton conductivity, and a catalyst. In the present invention, the ambient temperature molten salt may be used instead of at least one of the conductive material and the electrolyte material, and may be used in addition to the conductive material and the electrolyte material. The ambient temperature molten salt in the present invention is liquid at ambient temperature, thus hydrogen is occasionally taken in with difficulty, depending on the amount of the ambient temperature molten salt. In such a case, hydrogen is preferably supplied by bubbling.

Examples of the conductive material used for the electrode of the present invention include a carbon material. In addition, this carbon material may or may not have a porous structure, and preferably have a porous structure in the present invention. The reason therefor is that because of the large specific surface area, many reaction fields may be offered. Specific examples of the carbon material having a porous structure include mesoporous carbon. On the other hand, specific examples of the carbon material not having a porous structure include graphite, acetylene black, carbon nanotube and carbon fiber. Further, the content of the conductive material contained in the electrode varies greatly with kinds of the electrode and is not particularly limited.

Examples of the electrolyte material used for the electrode of the present invention include a solid electrolyte material and a polymer electrolyte material. Examples of the solid electrolyte material include a sulfide solid electrolyte material and an oxide solid electrolyte material. Examples of the sulfide solid electrolyte material having Li ion conductivity include a $Li_2S$—$P_2S_5$-based glassy sulfide solid electrolyte material. Further, examples of the polymer electrolyte material used for a fuel battery include a perfluorosulfonic acid-based polymer. Further, the content of the electrolyte material contained in the electrode varies greatly with kinds of the electrode and is not particularly limited.

The catalyst used for the electrode of the present invention is not particularly limited. Examples of the catalyst used for the air electrode of the metal air battery include inorganic ceramic materials such as $MnO_2$, $CeO_2$, $TiO_2$, $Co_3O_4$ and $Fe_3O_4$; organic complexes such as cobalt phthalocyanine and iron porphyrin; and composite materials thereof. Further, examples of the catalyst used for the electrode of a fuel battery include Pt. Further, the content of the catalyst contained in the electrode varies greatly with kinds of the electrode and is not particularly limited.

Examples of the binder used for the electrode of the present invention include fluorine-based binders such as polyvinylidene fluoride (PVDF) and polytetrafluorethylene (PTFE). Further, rubber such as SBR may be used as the binder. Further, the content of the binder contained in the electrode varies greatly with kinds of the electrode and is not particularly limited. Further, the thickness of the electrode of the present invention varies greatly with kinds of the electrode and is not particularly limited.

C. Battery

Next, a battery of the present invention is described. The battery of the present invention is a battery comprising a first electrode, a second electrode, and an electrolyte layer formed between the first electrode and the second electrode, characterized in that at least one of the first electrode and the second electrode is the above-described electrode, and the electrolyte layer does not transmit the ambient temperature molten salt contained in the electrode.

According to the present invention, the use of the electrode containing the ambient temperature molten salt allows a battery small in internal resistance.

Figure 3:
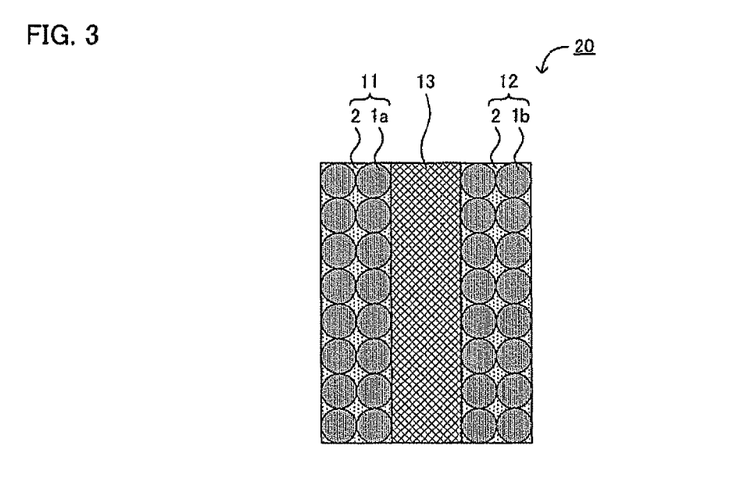
FIG. 3 is a schematic cross-sectional view showing an example of a generating element of a battery of the present invention.

FIG. 3 is a schematic cross-sectional view showing an example of a generating element of the battery of the present invention. A generating element 20 shown in FIG. 3 comprises a first electrode 11 containing an active material 1a and an ambient temperature molten salt 2, a second electrode 12 containing an active material 1b and the ambient temperature molten salt 2, and an electrolyte layer 13 formed between the first electrode 11 and the second electrode 12, which does not transmit the ambient temperature molten salt 2.

The battery of the present invention is hereinafter described in each constitution.

1. First Electrode and Second Electrode

In the present invention, at least one of the first electrode and the second electrode is the electrode described in the 'B. Electrode'. Such an electrode is as described above; therefore, the description herein is omitted.

2. Electrolyte Layer

Next, an electrolyte layer in the present invention is described. The electrolyte layer in the present invention is formed between the first electrode and the second electrode, and does not transmit the ambient temperature molten salt contained in the electrode for preventing an internal short circuit. The electrolyte layer in the present invention is not particularly limited if it has predetermined ion conductivity and does not transmit the ambient temperature molten salt contained in the electrode; examples thereof include a solid electrolyte layer having such denseness that does not allow the ambient temperature molten salt to transmit, a polymer electrolyte layer having such denseness that does not allow the ambient temperature molten salt to transmit, and a liquid electrolyte incompatible with the ambient temperature molten salt, above all, preferably the solid electrolyte layer having such denseness that does not allow the ambient temperature molten salt to transmit. The reason therefor is that it allows the battery high in safety.

The solid electrolyte layer is a layer containing at least a solid electrolyte material. In addition, a binder may be contained therein for improving denseness. The solid electrolyte layer which does not transmit the ambient temperature molten salt may be obtained by adding the binder to produce the sheet-like solid electrolyte layer. Simply, the pressure molding of the solid electrolyte material allows the solid electrolyte layer excellent in denseness. Kinds of the solid electrolyte material used for the solid electrolyte layer are not particularly limited as long as it has predetermined ion conductivity. Examples of the solid electrolyte material include a sulfide solid electrolyte material and an oxide solid electrolyte material. Examples of the sulfide solid electrolyte material having Li ion conductivity include a $Li_2S$—$P_2S_5$-based glassy sulfide solid electrolyte material.

The polymer electrolyte layer is a layer containing at least a polymer electrolyte material. In addition, a binder may be contained therein for improving denseness. Kinds of the polymer electrolyte material used for the polymer electrolyte layer are not particularly limited if it has predetermined ion conductivity. Examples of the polymer electrolyte material used for the polymer electrolyte layer of a fuel battery include a perfluorosulfonic acid-based polymer.

The liquid electrolyte is not particularly limited if it is incompatible with the ambient temperature molten salt, and a general liquid electrolyte may be used. Further, the liquid electrolyte ordinarily contains a metal salt and a solvent. Examples of a lithium salt include inorganic lithium salts such as $LiPF_6$, $LiBF_4$, $LiClO_4$ and $LiAsF_6$, and organic lithium salts such as $LiCF_3SO_3$, $LiN(CF_3SO_2)_2$, $LiN(C_2F_5SO_2)_2$ and $LiC(CF_3SO_2)_3$. On the other hand, water or a nonaqueous solvent is selected for the solvent in accordance with kinds of the salt. Examples of the nonaqueous solvent include ethylene carbonate (EC), propylene carbonate (PC), dimethyl carbonate (DMC), diethyl carbonate (DEC), ethyl methyl carbonate (EMC), butylene carbonate (BC), and optional mixtures thereof. Further, the liquid electrolyte may be used while being impregnated into a separator.

3. Other Constitutions

The battery of the present invention may have a current collector for collecting the first electrode, a current collector for collecting the second electrode, a battery case and a separator and the like in addition to the first electrode, second electrode and electrolyte layer. A material for the current collector is not particularly limited and examples thereof include copper, stainless steel, nickel and carbon. Further, the shape of the battery case is not particularly limited and examples thereof include a coin shape, a laminate shape, a cylindrical shape and a rectangular shape. Further, kinds of the battery of the present invention are not particularly limited and the description is the same as that described in the 'A. Ambient temperature molten salt'.

D. Agent for Preventing Charge-Up

Next, an agent for preventing a charge-up of the present invention is described. The agent for preventing a charge-up of the present invention comprises the above-described ambient temperature molten salt.

According to the present invention, the inclusion of the ambient temperature molten salt allows an agent for preventing a charge-up to have excellent electron conductivity. Thus, the effect of preventing a charge-up is high, therefore, building up an electric charge in a measuring object and occurrence of a charge-up can be prevented even in long-time continuous measurement. Further, the agent for preventing a charge-up of the present invention may take an optional shape by reason for that it is ordinarily liquid, and has the advantage that grounding for preventing a charge-up from occurring is easy. In addition, since the ambient temperature molten salt used for the present invention is high in nonvolatility, it becomes to act as the useful agent for preventing a charge-up in measuring a measuring object which is difficult to subject for atmospheric exposure. Similarly, the ambient temperature molten salt used for the present invention is high in nonvolatility, thus the measurement may be performed in the same state as the case where moisture is retained by replacing the moisture of a measuring object retaining the moisture with the ambient temperature molten salt.

The agent for preventing a charge-up of the present invention contains at least the ambient temperature molten salt described in the 'A. Ambient temperature molten salt'. In addition, the agent for preventing a charge-up of the present invention may contain a dilution solvent for diluting the ambient temperature molten salt as required. The reason therefor is that the use of the dilution solvent allows the agent for preventing a charge-up to be uniformly impregnated into a measuring object having a microstructure. The dilution solvent is not particularly limited if it may dilute the ambient temperature molten salt, and may be an organic solvent or an inorganic solvent. Examples of the dilution solvent include alcohol, benzene, toluene, acetone, methyl ethyl ketone, methylene chloride, chloroform, carbon tetrachloride, tetrahydrofuran, dioxane, pentane, and hexane.

Further, the agent for preventing a charge-up of the present invention preferably has the property of not substantially volatilizing in a vacuum. The reason therefor is that that may allow the useful agent for preventing a charge-up in a measuring method for which a vacuum needs to be formed. The phrase 'the property of not substantially volatilizing' signifies that nonvolatility that does not hinder measurement is exhibited in a vacuum.

The uses of the agent for preventing a charge-up of the present invention are not particularly limited if they are used for preventing a measuring object from becoming charged; specific examples thereof include a use for measurement by an electron microscope, and a use for measurement by an X-ray photoelectron spectroscopy (XPS). Above all, the agent for preventing a charge-up of the present invention is preferably used for measurement by an electron microscope. Kinds of the electron microscope are not particularly limited if it causes the charge-up, and examples thereof include a scanning electron microscope (SEM) and a transmission electron microscope (TEM).

E. Method for Observing Sample

Next, a method for observing a sample of the present invention is described. The method for observing a sample of the present invention is a method for observing, in which a sample has a measuring object and an agent for preventing a charge-up which prevents a charge-up of the measuring object and is observed by an electron microscope, characterized in that the agent for preventing a charge-up is the above-described agent for preventing a charge-up.

According to the present invention, the use of the agent for preventing a charge-up may efficiently prevent a charge-up from occurring. In particular, in long-time continuous measurement, an electric charge may be prevented from building up in the measuring object and a charge-up may be prevented from occurring. Further, conventionally, in order to impart electron conductivity to the measuring object, carbon, aluminum and platinum have been deposited to prevent a charge-up; however, the present invention has the advantage that a charge-up may be easily prevented without performing such a deposition process.

The sample used for the present invention ordinarily has the measuring object and the agent for preventing a charge-up. The measuring object is ordinarily a member low in electron conductivity, specifically an insulating member. Further, the measuring object used for the present invention is preferably an object that is difficult to subject for atmospheric exposure. Since the nonvolatility of the agent for preventing a charge-up is high, the measurement may be performed in an air atmosphere even in the case of using such a measuring object. The measuring object which is difficult to subject for atmospheric exposure signifies the measuring object which reacts with an atmospheric component (such as water) to change in quality. Further, the measuring object used for the present invention is preferably a member used for a battery. Examples of the member used for a battery include a member containing at least one of a positive active material, a negative active material and a solid electrolyte material. Other examples of the member used for a battery include a member containing at least one of a positive active material layer, a solid electrolyte layer and a negative active material layer. Above all, in the present invention, the measuring object is preferably a member having at least a solid electrolyte layer, which preferably contains a sulfide solid electrolyte material. The reason therefor is that the sulfide solid electrolyte material occasionally reacts with moisture in the air to produce hydrogen sulfide.

Further, the agent for preventing a charge-up used for the present invention is the same as that described in the 'D. Agent for preventing charge-up'; therefore, the description herein is omitted. Further, the agent for preventing a charge-up prevents a charge-up of the measuring object and may contact with at least part of the measuring object, more preferably the wider areas of the measuring object. The reason therefor is that a charge-up may be efficiently prevented.

Next, a method for producing a sample in the present invention is described. In the present invention, an optional method for producing a sample may be used if the above-described sample may be obtained. Basically, a desired sample may be obtained by adding the agent for preventing a charge-up to the measuring object. Further, the agent for preventing a charge-up may be applied to or impregnated into the measuring object, and the measuring object may be immersed in the agent for preventing a charge-up. Further, in the case where the agent for preventing a charge-up contains the above-described dilution solvent, the agent for preventing a charge-up is preferably added to the measuring object to thereafter remove the dilution solvent. Further, in the case of using the measuring object retaining a moisture, it is preferable that the moisture contained in the measuring object is replaced with the ambient temperature molten salt by adding the agent for preventing a charge-up to the measuring object, and thereafter the moisture is removed.

Further, kinds of the electron microscope used for the present invention are not particularly limited if it causes the charge-up, and examples thereof include a scanning electron microscope (SEM) and a transmission electron microscope (TEM).

F. Electrode

Next, an electrode of the present invention is described. The electrode of the present invention comprises a liquid electron/ion conductor and an active material capable of supplying or receiving a metal ion.

According to the present invention, the use of the liquid electron/ion conductor as a conductive assistant (a conductive material) may prevent an electron conduction path from being cut by expansion or contraction of the active material, and may improve cycling characteristics. Conventionally, it has not been known that the liquid electron/ion conductor is used as the conductive assistant. On the contrary, the present invention adopts a new constitution that the liquid electron/ion conductor is used as the conductive assistant such that an electron conduction path can be prevented from being cut by expansion or contraction of the active material. This effect is the same as that described in the FIGS. 2A and 2B.

The liquid electron/ion conductor in the present invention is liquid in a working temperature region of the electrode. In the case where the electrode of the present invention is used for a battery, the liquid electron/ion conductor in the present invention is ordinarily liquid in a working temperature region of the battery. The working temperature region of the battery varies with kinds of the battery, preferably within a range of $-30°$ C. to $150°$ C., for example.

Further, the liquid electron/ion conductor is preferably the ambient temperature molten salt. The reason therefor is that it is excellent in nonvolatility and voltage endurance. The ambient temperature molten salt is not particularly limited if it has desired electron conductivity and ion conductivity, and examples thereof include the ambient temperature molten salt described in the 'A. Ambient temperature molten salt'.

Further, the electric current density of the liquid electron/ion conductor is, for example, preferably $0.5 \times 10^{-5}$ A/cm$^2$ or more, more preferably $1.0 \times 10^{-5}$ A/cm$^2$ or more, and far more preferably $1.0 \times 10^{-4}$ A/cm$^2$ or more. Further, the ion conductivity (ambient temperature) of the liquid electron/ion conductor is, for example, preferably $1 \times 10^{-6}$ S/cm or more, more preferably $1 \times 10^{-5}$ S/cm or more, and far more preferably $1 \times 10^{-4}$ S/cm or more.

Further, the active material in the present invention is the same as that described in the 'B. Electrode'. The electrode of the present invention may further contain at least one selected from the group consisting of a catalyst for accelerating a reaction in the electrode, a conductive material having electron conductivity, an electrolyte material having ion conductivity (such as a solid electrolyte material), and a binder. The uses of these material and electrode are the same as those described in the 'B. Electrode'. Further, the present invention may provide a battery having the electrode. The battery is the same as that described in the 'C. Battery'.

The present invention is not limited to the embodiments. The embodiments are exemplification, and any embodiment is included in the technical scope of the present invention if it has substantially the same constitution as the technical idea described in the claims of the present invention and achieves similar operation and effect thereto.

EXAMPLES

The present invention is hereinafter described more specifically while showing examples.

Example 1

Solid EMImCl and FeCl$_3$ at ambient temperature were weighed so as to be EMImCl:FeCl$_3$=1:1 (molar ratio), both mixed under an Ar atmosphere and melted uniformly to thereby obtain EMImFeCl$_4$ (a melting point of $18°$ C.) as an ambient temperature molten salt. Next, solid EMImCl at ambient temperature and the obtained EMImFeCl$_4$ were weighed so as to be EMImCl:EMImFeCl$_4$=2:10 (molar ratio), both mixed under an Ar atmosphere and melted uniformly to thereby obtain an ambient temperature molten salt (10EMImFeCl$_4$+2EMImCl).

Example 2

An ambient temperature molten salt (10EMImFeCl$_4$+5EMImCl) was obtained in the same manner as Example 1 except for modifying the ratio of EMImCl and EMImFeCl$_4$ into EMImCl:EMImFeCl$_4$=5:10 (molar ratio).

Example 3

An ambient temperature molten salt (10EMImFeCl$_4$+10EMImCl) was obtained in the same manner as Example 1 except for modifying the ratio of EMImCl and EMImFeCl$_4$ into EMImCl:EMImFeCl$_4$=10:10 (molar ratio).

Comparative Example 1

EMImFeCl$_4$ produced in Example 1 was regarded as a comparison sample.

Comparative Example 2

0.01-M NaCl aqueous solution was regarded as a comparison sample.

[Evaluation 1]

Figure 4:
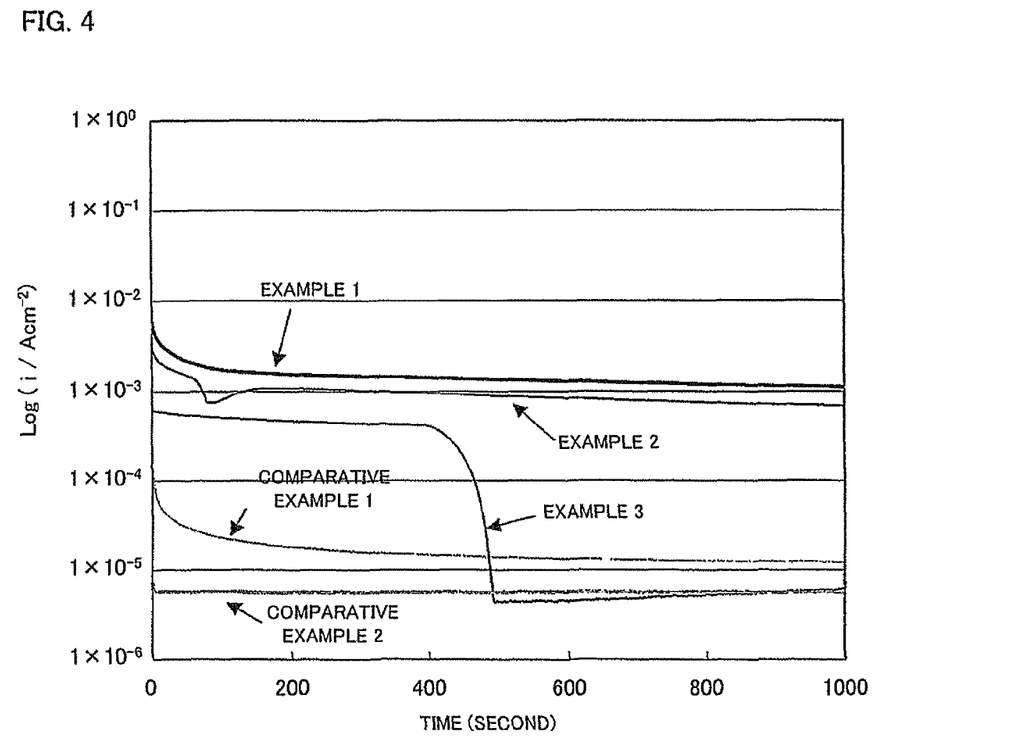
FIG. 4 is a result of measuring electron conductivity of a sample each obtained in Examples 1 to 3 and Comparative Examples 1 and 2.

Electron conductivity of the samples obtained in Examples 1 to 3 and Comparative Examples 1 and 2 was evaluated. Specifically, φ-1.5 mm Ni electrode was immersed by two pieces in the samples to perform constant-potential measurement at a voltage of 0.1V. The results are shown in FIG. 4. As shown in FIG. 4, it was confirmed that electron conductivity (electric current density) improved dramatically in Examples 1 to 3 compared with Comparative Examples 1 and 2 (particularly, Comparative Example 1). In Example 3, the deterioration of electron conductivity was observed in the course of measurement, while approximately constant electron conductivity was exhibited for at least 1 hour in Examples 1 and 2. Through the above, it was confirmed that the ambient temperature molten salt of the present invention had excellent electron conductivity.

Comparative Example 3

PP13TFSA (N-methyl-N-propylpiperidinium bistrifluoromethanesulfonylamido) was regarded as a comparison sample.

[Evaluation 2]

Figure 5:
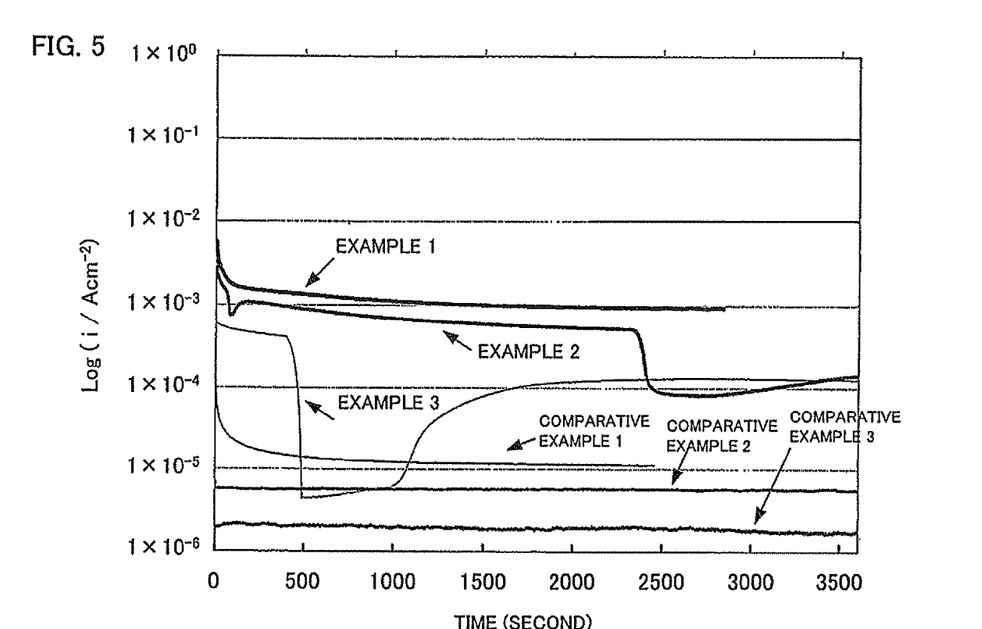
FIG. 5 is a result of measuring electron conductivity of a sample each obtained in Examples 1 to 3 and Comparative Examples 1 to 3.

Electron conductivity of the samples obtained in Examples 1 to 3 and Comparative Examples 1 to 3 was evaluated. Specifically, φ-1.5 mm Ni electrode was immersed by two pieces in the samples to perform constant-potential measurement at a voltage of 0.1V. The results are shown in FIG. 5. In FIG. 5, the measuring time is longer than FIG. 4. As shown in FIG. 5, in Example 3, it was confirmed that electron conductivity deteriorated once and yet recovered thereafter. Similarly, in Example 2, it was confirmed that electron conductivity deteriorated once and yet recovered thereafter. On the other hand, in Example 1, the deterioration in electron conductivity was not confirmed. Further, in Comparative Example 3, it was confirmed that electron conductivity of PP13TFSA as an ambient temperature molten salt was low.

Example 4

EMImCl and $CrCl_3$ as a metal chloride were weighed so as to be EMImCl:$CrCl_3$=12:10 (molar ratio), both mixed under an Ar atmosphere and melted uniformly to thereby obtain an ambient temperature molten salt (10EMTmCrCl$_4$+2EMImCl).

Example 5

EMImCl and $VCl_3$ as a metal chloride were weighed so as to be EMImCl:$VCl_3$=12:10 (molar ratio), both mixed under an Ar atmosphere and melted uniformly to thereby obtain an ambient temperature molten salt (10EMImVCl$_4$+2EMImCl).

Example 6

$FeCl_3$ and LiCl as metal chlorides were weighed so as to be $FeCl_3$: LiCl=10:0.2 (molar ratio), and stirred uniformly in ethanol of the same weight as $FeCl_3$. Thereafter, EMImCl of the same weight as $FeCl_3$ was added to the ethanol solution to remove the ethanol at a temperature of 60° C. and then obtain an ambient temperature molten salt (10EMImFeCl$_4$+0.2LiCl).

[Evaluation 3]

Figure 6:
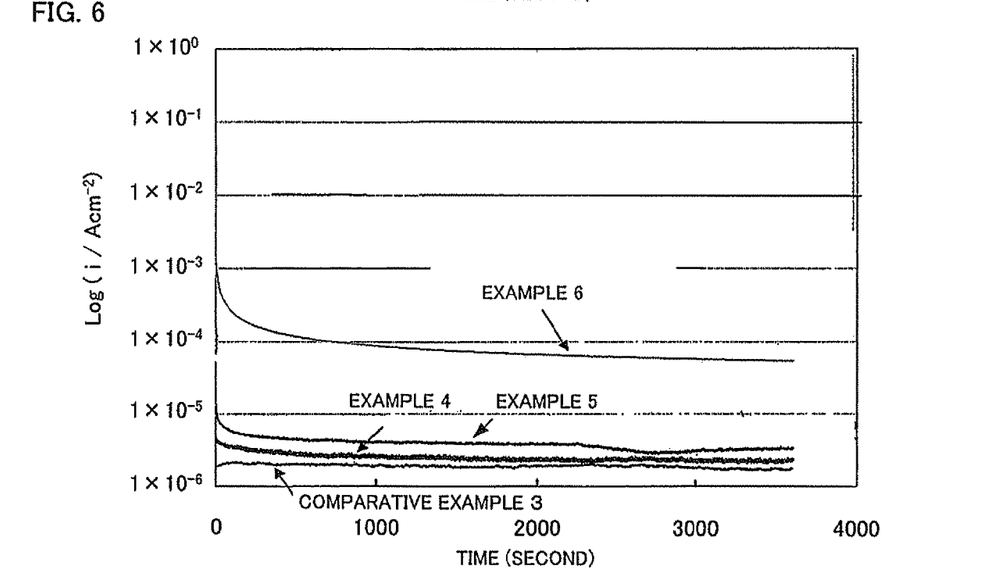
FIG. 6 is a result of measuring electron conductivity of a sample each obtained in Examples 4 to 6 and Comparative Example 3.

Electron conductivity of the samples obtained in Examples 4 to 6 and Comparative Example 3 was evaluated. Specifically, φ-1.5 mm Ni electrode was immersed by two pieces in the samples to perform constant-potential measurement at a voltage of 0.1 V. The results are shown in FIG. 6. As shown in FIG. 6, it was confirmed that electron conductivity (electric current density) improved in Examples 4 to 6 compared with Comparative Example 3.

Example 7

Solid EMImBr and $FeBr_3$ at ambient temperature were weighed so as to be EMImBr:$FeBr_3$=12:10 (molar ratio), both mixed under an Ar atmosphere and melted uniformly to thereby obtain an ambient temperature molten salt (10EMImFeBr$_4$+2EMImBr).

[Evaluation 4]

Figure 7:
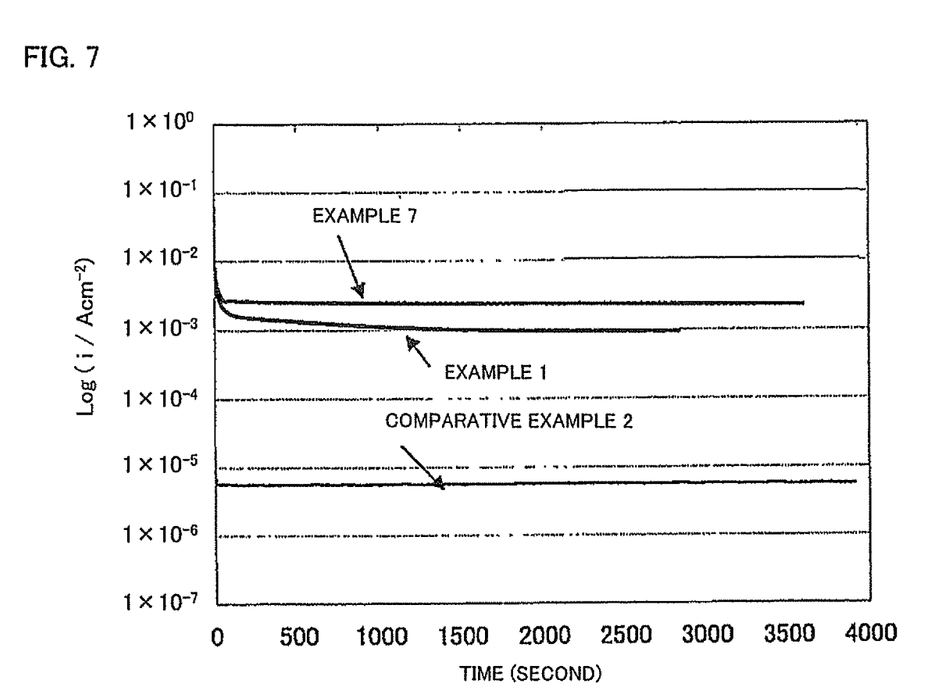
FIG. 7 is a result of measuring electron conductivity of a sample each obtained in Examples 1 and 7 and Comparative Example 2.

Electron conductivity of the samples obtained in Examples 1 and 7 and Comparative Example 2 was evaluated. Specifically, φ-1.5 mm Ni electrode was immersed by two pieces in the samples to perform constant-potential measurement at a voltage of 0.1 V. The results are shown in FIG. 7. As shown in FIG. 7, it was confirmed that electron conductivity (electric current density) improved in Example 7 as compared with Example 1 and Comparative Example 2.

REFERENCE SIGNS LIST

1 Active material
2 Ambient temperature molten salt
3 Conductive material
10 Electrode
11 First electrode
12 Second electrode
13 Electrolyte layer
20 Generating element

The invention claimed is:

1. A battery, comprising:
a first electrode;
a second electrode; and
an electrolyte layer formed between the first electrode and the second electrode,
wherein:
at least one of the first electrode and the second electrode is an electrode comprising an ambient temperature molten salt;
the electrolyte layer does not transmit the ambient temperature molten salt contained in the electrode;
the ambient temperature molten salt comprises:
a first imidazolium salt having a cationic segment represented by the following General Formula (1) and an anionic segment represented by $MX_4$, wherein M is at least one element selected from the group consisting of Fe, Cr, V, Co, Mn, Ti, Ru, and Pb, and X is F, Cl, Br, or I; and
a second salt having a cationic segment represented by the following General Formula (2) or a cationic segment which is Li, Na, or K, and an anionic segment represented by X, wherein X is F, Cl, Br, or I, General Formula (1)

General Formula (2)

wherein:
in the General Formula (1), $R_1$ and $R_2$ are each an alkyl group with a carbon number of 1 to 10, and
in the General Formula (2), $R_3$ and $R_4$ are each an alkyl group with a carbon number of 1 to 10; and
a content of the second salt in the ambient temperature molten salt is 10 parts by mol or more and 50 parts by mol or less with respect to 100 parts by mol of the first imidazolium salt.

2. The battery according to claim 1, wherein:
in the first imidazolium salt:
M is Cr, V, Co, Mn, Ti, Ru, or Pb.

3. The battery according to claim 1, wherein:
in the first imidazolium salt:
X is F, Br, or I.

4. The battery according to claim 1, wherein:
in the first imidazolium salt:
- M is Fe, Cr, or V,
- X is Cl or Br; and in the second salt:
- the cationic segment is Li, and
- X is Cl or Br.

5. The battery according to claim 1, wherein:
in the first imidazolium salt:
- M is Cr or V,
- X is Cl or Br; and in the second salt:
- the cationic segment is represented by General Formula (2) or Li, and
- X is Cl or Br.

6. The battery according to claim 1, wherein:
in the first imidazolium salt:
- M is Fe, Cr, or V,
- X is Br; and in the second salt:
- the cationic segment is represented by General Formula (2) or Li, and
- X is Cl or Br.

7. The battery according to claim 1, wherein:
in the first imidazolium salt:
- M is Fe, Cr, or V,
- X is Cl or Br; and in the second salt:
- the cationic segment is represented by General Formula (2) or Li, and
- X is Br.

8. The battery according to claim 1, wherein:
the first imidazolium salt is $EMImFeCl_4$, $EMImCrCl_4$, $EMImVCl_4$, or $EMImFeBr_4$, and
the second salt is EMImCl, EMImBr, or LiCl.

9. The battery according to claim 1, wherein at least one of the first electrode and the second electrode, which comprises the ambient temperature molten salt, further comprises an active material capable of supplying or receiving a metal ion.

10. The battery according to claim 1, wherein the electrolyte layer is a solid electrolyte layer having a denseness that does not allow the ambient temperature molten salt to transmit.

11. The battery according to claim 1, wherein the battery is an Li ion battery.

* * * * *